United States Patent [19]

Hübner et al.

[11] 4,107,103
[45] Aug. 15, 1978

[54] POLYURETHANES PRODUCED FROM PHOSPHORUS CONTAINING FLAME RETARDING AGENTS WHICH ARE REACTIVE WITH ISOCYANATES

[75] Inventors: Hans Hübner, Leverkusen; Johannes Blahak, Cologne; Hans-Joachim Meiners, Leverkusen, Germany

[73] Assignee: Bayer Aktiengesellschaft, Leverkusen, Fed. Rep. of Germany

[21] Appl. No.: 836,189

[22] Filed: Sep. 26, 1977

Related U.S. Application Data

[62] Division of Ser. No. 637,799, Dec. 4, 1975, abandoned.

[30] Foreign Application Priority Data

Dec. 17, 1974 [DE] Fed. Rep. of Germany ........ 2459492

[51] Int. Cl.² .................... C08G 18/32; C08G 18/38
[52] U.S. Cl. ................................... 528/72; 544/195; 521/165
[58] Field of Search ............... 260/2.5 AM, 77.5 AM, 260/2.5 AJ, 75 NQ

[56] References Cited

U.S. PATENT DOCUMENTS

| | | | |
|---|---|---|---|
| 3,121,082 | 2/1964 | Guttag | 260/2.5 AN |
| 3,210,350 | 10/1965 | D'Alelio | 260/248 |
| 3,364,216 | 1/1968 | Johnson | 260/2.5 AJ |
| 3,551,422 | 12/1970 | Tesoro | 260/249.9 |

*Primary Examiner*—C. Warren Ivy
*Attorney, Agent, or Firm*—Gene Harsh; Joseph C. Gil; William E. Parry

[57] ABSTRACT

This invention relates to novel halogen-free flame retarding agents and a process in which they are used in the production of polyurethanes. These compounds are represented by the general formula:

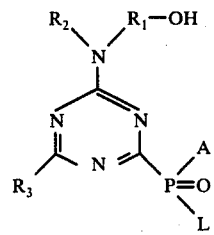

wherein:
$R_1$ represents $C_1$–$C_5$ alkylene groups which may be branched,
$R_2$ represents $C_1$–$C_3$ alkyl groups which may be branched or $R_1OH$ and
$R_3$ represents $C_1$–$C_8$-alkyl, $C_1$–$C_8$-dialkylamino, $C_1$–$C_4$-oxyalkyl, $C_1$–$C_4$-thioslkyl, $C_6$–$C_{14}$-aryl or $C_7$–$C_{15}$-aralkyl groups or

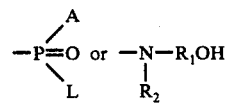

and
A and L may be identical or different and represent $C_1$–$C_{10}$-alkyl groups, which may be branched, benzyl groups or OR groups, wherein
R represents an alkyl group, with 1–8 C atoms which may be branched, or a benzyl group.

6 Claims, No Drawings

POLYURETHANES PRODUCED FROM PHOSPHORUS CONTAINING FLAME RETARDING AGENTS WHICH ARE REACTIVE WITH ISOCYANATES

This is a division of application Ser. No. 637,799 filed Dec. 4, 1975, now abandoned.

BACKGROUND OF THE INVENTION

It is known that the flame resistance of synthetic resins, in particular polyurethanes resins, can be increased by the addition of unreactive low molecular weight phosphoric or phosphonic acid esters during the manufacturing process. This procedure is, however, limited by the fact that if the desired mechanical properties are to be obtained, these low molecular weight compounds may only be used in such limited quantities that they are insufficient to ensure complete flame resistance. The procedure is also limited by the fact that these additives tend to migrate from the resin, because of their low molecular weight.

Attempts have been made to overcome this difficulty by incorporating halogen containing polycarboxylic acids or polyhydroxyl compounds into the molecular structure. Such halogenated components include tetrachlorophthalic acid, dibromophthalic acid or hexachloroendomethylene tetrahydrophthalic acid. Polyesters produced from such components have a much improved flame resistance (e.g. after they have been foamed with polyisocyanates), but such resistance is still insufficient in many cases. Other disadvantages lie in the fact that these polyesters are difficult to mix with polyisocyanates at room temperature because of their high viscosity, so that processing difficulties arise during the production of foams. Moreover, these polyesters tend to give rise to brittle foams when reacted with polyisocyanates so that they can only be converted into foams of satisfactory mechanical quality if they are mixed with the usual polyesters. In that case, however, the flame resistance achieved is partly lost. Furthermore, many of the conventional halogen containing flame retarding agents liberate corrosive gases such as hydrogen chloride or hydrogen bromide on combustion.

Flame resistant polyurethane resins which have good mechanical properties are obtained when using polyisocyanates which contain phosphoric acid or thiophosphoric acid groups (for example, the p-isocyanatophenyltriester of phosphoric acid). Phosphoric ester triisocyanates, however, can only be obtained by multistage processes and their use is therefore often uneconomical.

Hydrocarbon phosphonyl diisocyanates have also been used for the production of flame resistant foams. These diisocyanates, however, are acyl isocyanates, which are not only physiologically unpleasant because of their odor and vapor pressure but also because they are excessively reactive and readily saponified. Satisfactory foams, then, can only be obtained using usch isocyanates if the isocyanates are mixed with considerable quantities of the usual polyisocyanates such as tolylene diisocyanate. It is obvious, however, that the flame retarding properties are then lost.

The use of phosphorus containing polyether and polyester polyols for the production of polyurethane foams is also known in the art. These products, however, give rise to copious production of fumes when subjected to heat. Moreover, they are in many cases difficult to handle because of their viscosity which may interfere with the foaming process.

DESCRIPTION OF THE INVENTION

It has now been found that non-flammable or substantially non-flammable polyurethane resins can be obtained without the disadvantages of the known flame retarding agents described above if novel polyols which contain a phosphorus substituted s-triazine ring are used as reactants in the preparation of the polyurethane.

This invention relates to flame retarding agents of the following general formula which are free from halogen groups and which are reactive with isocyanates:

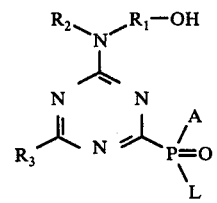

in which:
$R_1$ represents optionally branched $C_1$–$C_5$ alkyl groups,
$R_2$ represents optionally branched $C_1$–$C_5$ alkyl groups or $R_1OH$ and
$R_3$ represents $C_1$–$C_8$-alkyl, $C_1$–$C_8$-dialkylamino, $C_1$–$C_4$-oxyalkyl, $C_1$–$C_4$-thioalkyl, $C_6$–$C_{14}$-aryl, $C_7$–$C_{15}$-aralkyl groups, or, preferably

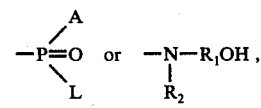

wherein
A and L which may be identical or different, represent optionally branched $C_1$–$C_{10}$-alkyl groups, benzyl or, preferably, the group OR wherein R denotes an optionally branched alkyl group containing 1 – 8, and preferably 1 – 4 C atoms, or a benzyl group.

The compounds according to the invention are prepared by a two-stage or three-stage substitution of the halogen atoms of cyanuric chloride or cyanuric fluoride in any sequence.

Either the groups

and optionally $R_3$ are successively introduced into the compounds

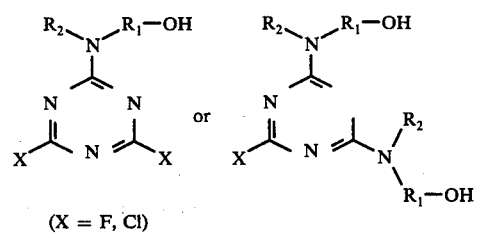

(X = F, Cl)

which are suspended in inert organic solvents such as acetylene tetrachloride, methyl chloroform, pentachloroethane or liquid hydrocarbons, such as toluene or dichloroethane, or the following compounds are first synthesized:

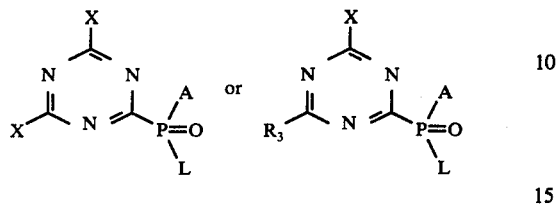

and then reacted with alkanolamines of the general formula

A, L, $R_1$, $R_2$ and $R_3$ having the same meaning as above.

The reaction between the halogen attached to the triazine ring and compounds of the general formula:

in which A, L and R have the meaning defined above (phosphorus, phosphonous or phosphinous acid ester) proceeds in a manner analogous to the known Michaelis-Arbusov reaction, preferably in the one of the inert solvents mentioned above, and results in almost quantitative yields at temperatures of 50° to 150° C, preferably 70° to 130° C. The reaction can be controlled by suitable choice of the molar quantities of starting components so that either one or two of the halogen atoms attached to the s-triazine ring can be substituted by

The process of the reaction can easily be followed by collecting the RX formed during the Michaelis-Arbusov reaction and measuring it volumetrically, e.g. by means of a gas meter.

Introduction of the substituents $R_3$ and

into the s-triazine ring is carried out by methods known per se. Reference is made to J. T. Thurston et al. in J. Amer. Chem. Soc. 73, 2983(1951).

The following are typical examples of compounds according to the invention:

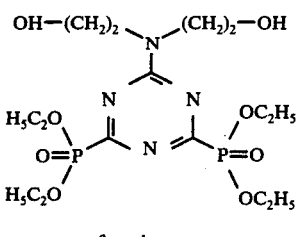

preferred

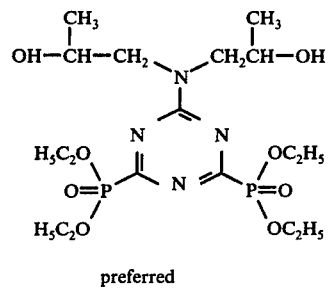

preferred

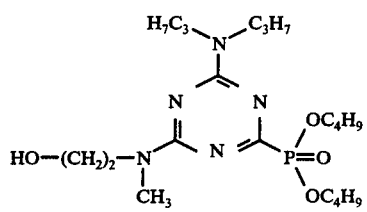

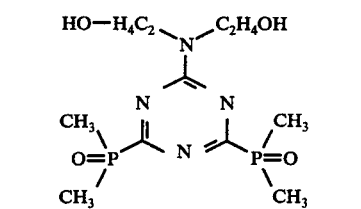

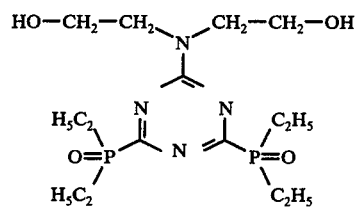

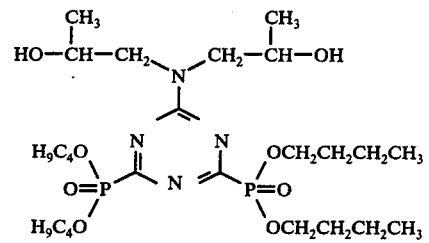

preferred

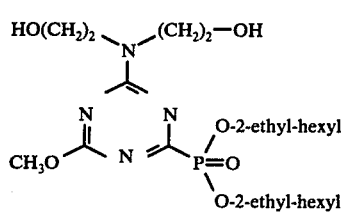

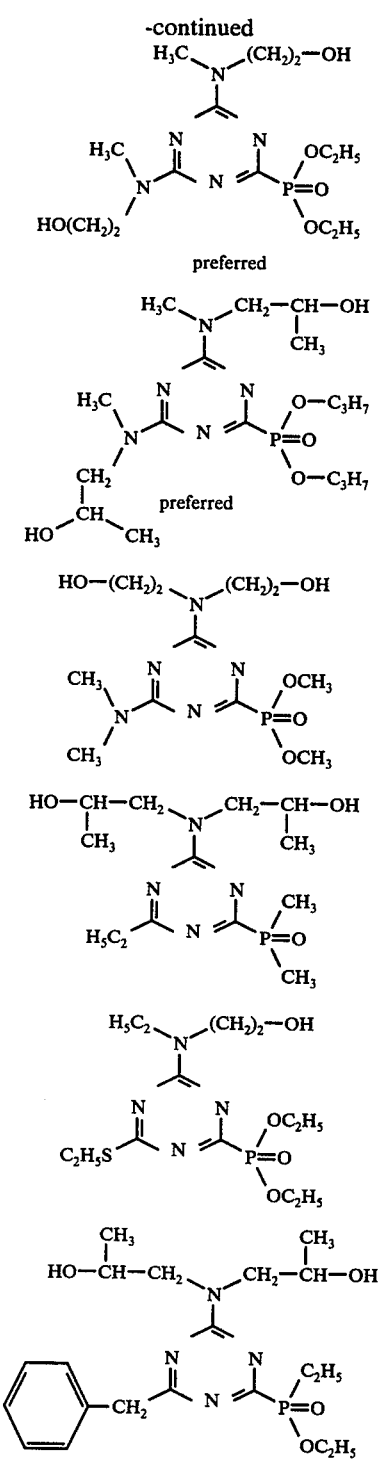

The phosphorus containing polyols according to the invention are used as reactants together with polyisocyanates, other high molecular weight and/or lower molecular weight polyols and optionally other compounds containing groups which are reactive with isocyanates, for the production of polyurethanes, such as, lacquers, foils, coatings, elastomers and fillers, but preferably polyurethane foams. In order to ensure sufficient flame resistance, the polyols according to the invention are used in a quantity such that the finished polyurethane resin contains at least 0.5% by weight phosphorus.

This invention therefore also relates to a process for the preparation of polyurethanes from polyisocyanates, high molecular weight and/or low molecular weight polyols and optionally other compounds containing groups which are reactive with isocyanates, characterized in that compounds of the following general formula which are reactive with isocyanates:

wherein:
A, L, $R_1$, $R_2$ and $R_3$ have the meanings defined above, are used in such a quantity that the polyurethane contains at least 0.5% by weight of phosphorus.

The simplest technical method of producing polyurethane foams consists of mixing the compounds of the invention, either alone or together, with other polyol components (polyethers or polyesters). These polyol mixtures, together with the foam activators, catalysts, blowing agents, mold release agents, pore regulators, emulsifiers and other auxiliary agents, are mixed with the isocyanate component. This reaction mixture is then foamed either freely or in a closed mold to form an integral foam having a non-cellular skin and cellular core. The formulations of the reaction mixtures are adjusted so that the effective phosphorus content is 0.5 to 10% by weight, preferably 1 to 4% by weight, based on the total mixture.

The isocyanates used as starting components according to the invention may be aliphatic, cycloaliphatic, araliphatic, aromatic or heterocyclic polyisocyanates such as those described e.g. by W. Siefken in Justus Liebigs Annalen der Chemie, 562, pages 75 to 136. Examples include ethylene diisocyanate; tetramethylene-1,4-diisocyanate; hexamethylene-1,6-diisocyanate; dodecane-1,12-diisocyanate; cyclobutane-1,3-diisocyanate; cyclohexane-1,3- and 1,4-diisocyanate and mixtures of these isomers; 1-isocyanato-3,3,5-trimethyl-5-isocyanatomethylcyclohexane as described in U.S. Pat. No. 3,401,190; hexahydrotolylene-2,4- and -2,6-diisocyanate and mixtures of these isomers; hexahydrophenylene-1,3- and/or 1,4-diisocyanate; perhydrodiphenylmethane-2,4'- and/or 4,4'-diisocyanate; phenylene-1,3- and -1,4-diisocyanate; tolylene-2,4- and -2,6-diisocyanate and mixtures of these isomers; diphenylmethane-2,4'- and/or 4,4'-diisocyanate; naphthylene-1,5-diisocyanate; triphenylmethane-4,4',4''-triisocyanate; polyphenyl-polymethylene polyisocyanates which can be obtained by aniline formaldehyde condensation followed by phosgenation as described in British Pat. Nos. 874,430 and 848,671; m- and p- isocyanatophenyl-sulphonylisocyanates as described in U.S. Pat. No. 3,454,606; perchlorinated aryl polyisocyanates as described in U.S. Pat. No. 3,277,138; polyisocyanates which contain carbodiimide groups as described in U.S. Pat. No. 3,152,162; diisocyanates as described in U.S. Pat. No. 3,492,330; polyisocyanates which contain allophanate groups as described in British Pat. No. 994,890, Belgian Pat. No. 761,626 and published Dutch Patent Application No. 7,102,524; polyisocyanates which contain isocyanurate groups as described in U.S. Pat. No. 3,001,973, German Pat. Nos. 1,022,789; 1,222,067 and 1,027,394 and German Offenlegungsschriften Nos. 1,929,034 and 2,004,048; polyisocyanates which contain urethane groups as described in Belgian Pat. No. 752,261 or U.S. Pat. No. 3,394,164; polyisocyanates which contain acylated urea groups as described in German Pat. No. 1,230,778; polyisocyanates which contain biuret groups as described in U.S. Pat. Nos. 3,124,605 and 3,201,372, and British Pat. No. 889,050; polyisocyanates prepared by telomerization reactions as described in U.S. Pat. No. 3,654,106; polyisocyanates which contain ester groups as described in British Pat. Nos. 965,474 and 1,072,956, U.S. Pat. No. 3,567,763 and German Pat. No. 1,231,688; and reaction products of the above mentioned isocyanates with acetals as described in German Pat. No. 1,072,385, as well as polyisocyanates which contain polymeric fatty acid groups as described in U.S. Pat. No. 3,455,883.

The distillation residues obtained from the commercial production of isocyanates which still contain isocyanate groups may also be used, if desired, as solutions in one or more of the above mentioned polyisocyanates. Any mixtures of the above mentioned polyisocyanates may also be used.

It is generally particularly preferred to use readily available polyisocyanates such as tolylene-2,4- and -2,6-diisocyanate and mixtures of these isomers ("TDI"), polyphenylpolymethylene-polyisocyanates which can be obtained by aniline formaldehyde condensation followed by phosgenation ("crude MDI"); and polyisocyanates which contain carbodiimide groups, urethane groups, allophanate groups, isocyanurate groups, urea groups or biuret groups ("modified polyisocyanates").

The starting components to be used according to the invention also include compounds which contain at least two hydrogen atoms capable of reacting with isocyanates, and which generally have a molecular weight of 400 to 10,000. Suitable compounds of this kind include not only compounds containing amino groups, thiol groups or carboxyl groups but also in particular polyhydroxyl compounds, and especially those containing two to eight hydroxyl groups and having a molecular weight of 600 to 8000, preferably 800 to 6000, such as polyesters, polyethers, polythioethers, polyacetals, polycarbonates or polyester amides containing at least 2, generally 2 to 8 but preferably 2 to 4 hydroxyl groups. These materials are of the kind which are known per se for the production both of homogeneous and of cellular polyurethanes.

The polyesters having hydroxyl groups which may be used as starting components include reaction products of polyhydric alcohols, preferably dihydric alcohols with the optional addition of trihydric alcohols, and polybasic, preferably dibasic carboxylic acids. Instead of free polycarboxylic acids, the corresponding polycarboxylic anhydrides or corresponding polycarboxylic acid esters of lower alcohols or their mixtures may be used for preparing the polyesters. The polycarboxylic acids may be aliphatic, cycloaliphatic, aromatic and/or heterocyclic and they may be substituted, e.g. with halogen atoms, and/or unsaturated. The following are examples: succinic acid, adipic acid, suberic acid, azelaic acid, sebasic acid, phthalic acid, isophthalic acid, trimetallic acid, phthalic acid anhydride, tetrahydrophthalic acid anhydride, hexahydrophthalic acid anhydride, tetrachlorophthalic acid anhydride, endomethylene tetrahydrophthalic acid anhydride, glutaric acid anhydride, maleic acid, maleic acid anhydride, fumaric acid, dimeric and trimeric fatty acids such as oleic acid, if desired mixed with monomeric fatty acids, dimethyl terephthalate or bis-glycol terephthalate. Suitable polyhydric alcohols include e.g. ethylene glycol, propylene-1,2- and -1,3-glycol , butylene-1,4- and -2,3-glycol, hexane-1,6-diol, octane-1,8-diol, neopentyl glycol, cyclohexane dimethanol (1,4-bis-hydroxy-methylcyclohexane), 2-methyl-propane-1,3-diol, glycerol, trimethylolpropane, hexane-1,2,6-triol, butane-1,2,4-triol, trimethylolethane, pentaerythritol, quinitol, mannitol and sorbitol, methyl glycoside, diethylene glycol, triethylene glycol, tetraethylene glycol, polyethylene glycols, dipropylene glycol, polypropylene glycols, dibutylene glycol and polybutylene glycols. The polyesters may also contain a proportion of carboxyl groups in end positions. Polyesters of lactones such as $\epsilon$-caprolactone or hydroxy-carboxylic acids such as $\omega$-hydroxycaproic acid may also be used.

The hydroxyl polyethers which may be used according to the invention and which contain at least two, generally two to eight, preferably two or three hydroxyl groups are also known per se, and are obtained, for example, by the polymerization of epoxides such as ethylene oxide, propylene oxide, butylene oxide, tetrahydrofuran, styrene oxide or epichlorohydrin, either alone, for example in the presence of $BF_3$, or by addition of these opoxides, optionally as mixtures or or successively, to starting components which contain reactive hydrogen atoms, such as water alcohols or amines, e.g. ethylene glycol, propylene-1,3- or -1,2-glycol, trimethylolpropane, 4,4'-dihydroxy-diphenylpropane, aniline, ammonia, ethanolamine and ethylene diamine. Sucrose polyethers as described in German Auslegeschriften Nos. 1,176,358 and 1,064,398 may also be used according to the invention. In many cases it is preferred to use polyethers of the kind which contain predominant amounts of primary OH groups (up to 90% by weight, based on all the OH groups present in the polyether). Polyethers which are modified with vinyl polymers, e.g. the compounds obtained by the polymerization of styrene and acrylonitrile in the presence of polyethers (U.S. Pat. Nos. 3,383,351; 3,304,273; 3,523,093 and 3,110,695, and German Pat. No. 1,152,536) are also suitable, as are polybutadienes which contain OH groups.

Suitable polythioethers include in particular the condensation products obtained from the condensation of thiodiglycol either on its own or with other glycols, dicarboxylic acids, formaldehyde, aminocarboxylic acids or amino alcohols. The products obtained are polythio mixed ethers, polythioether esters or polythioether ester amides, depending on the components.

Suitable polyacetals include e.g. the compounds which can be prepared from glycols such as diethylene glycol, triethylene glycol, 4,4'-dioxethoxy-diphenyldimethylmethane, hexanediol and formaldehyde. Polyacetals suitable for the purpose of the invention may also be prepared by the polymerization of cyclic acetals.

The polycarbonates having hydroxyl groups include those which can be prepared by the reaction of diols such as propane-1,3-diol, butane-1,4-diol and/or hexane-1,6-diol, diethylene glycol, triethylene glycol, or tetraethylene glycol, with diaryl carbonates, such as diphenylcarbonate, or phosgene.

Suitable polyester amides and polyamides include the predominantly linear condensates obtained from polybasic saturated and unsaturated carboxylic acids or their anhydrides and polybasic saturated and unsaturated amino alcohols, diamines, polyamines and mixtures thereof.

Polyhydroxyl compounds which already contain urethane or urea groups and modified or unmodified natural polyols such as castor oil, carbohydrates or starch may also be used. Addition products of alkylene oxides and phenol formaldehyde resins or urea formaldehyde resins may also be used according to the invention.

These types of compounds which can be used in the invention have been described in e.g. High Polymers Vol. XVI, "Polyurethanes, Chemistry and Technology" by Saunders-Frisch, Interscience Publishers, New York, London, Volume I, 1962, pages 32–42 and pages 44–54 and Volume II, 1964, pages 5–6 and 198–199, and Kunststoff-Handbuch, Volume VII, Vieweg-Hochtlen, Carl-Hanser-Verlag, Munich 1966, e.g. on pages 45 to 71.

The starting components used according to the invention may also include compounds having a molecular weight of 32 to 400 which contain at least two hydrogen atoms capable of reacting with isocyanates. These also are compounds containing hydroxyl groups and/or amino groups and/or thiol groups and/or carboxyl groups, preferably hydroxyl groups and/or amino groups, and they serve as chain lengthening agents or crosslinking agents. These compounds generally contain 2 to 8 hydrogen atoms capable of reacting with isocyanates, preferably two or three such hydrogen atoms. The following are examples of such compounds: Ethylene glycol, propylene-1,2- and -1,3-glycol, butylene-1,4- and -2,3-glycol, pentane-1,5-diol, hexane-1,6-diol, octane-1,8-diol, neopentyl glycol, 1,4-bis-hydroxymethylcyclohexane, 2-methyl-propane-1,3-diol, glycerol, trimethylol-propane, hexane-1,2,6-triol, trimethylolethane, pentaerythritol, quinitol, mannitol, sorbitol, diethylene glycol, triethylene glycol, tetraethylene glycol, polyethylene glycols having a molecular weight of up to 400, dipropylene glycol, polypropylene glycols having a molecular weight of up to 400, dibutylene glycol polybutylene glycols having a molecular weight of up to 400, 4,4'-dihydroxydiphenylpropane, dihydroxymethylhydroquinone, ethanolamine, diethanolamine, triethanolamine, 3-aminopropanol, ethylene diamine, 1,3-diaminopropane, 1-mercapto-3-aminopropane, 4-hydroxy- or -aminophthalic acid, succinic acid, adipic acid, hydrazine, N,N'-dimethylhydrazine and 4,4'-diaminodiphenylmethane.

Water and/or readily volatile organic substances may also be included as blowing agents according to the invention. Suitable organic blowing agents include acetone, ethyl acetate, halogenated alkanes such as methylene chloride, chloroform, ethylidene chloride, vinylidene chloride, monofluorotrichloromethane, chlorodifluoromethane or dichlorodifluoromethane, or butane, hexane, heptane or diethylether. The effect of a blowing agent may also be obtained by the addition of compounds which decompose at temperatures above room temperature to liberate gases. Such compounds include nitrogen, for example azo compounds such as azo isobutyric acid nitrile. Other examples of blowing agents and details concerning the use of blowing agents may be found in Kunststoff-Handbuch, Volume VII, published by Vieweg and Hochtlen, Carl-Hanser-Verlag, Munich 1966, e.g. on pages 108 to 109, 453 to 455 and 507 to 510.

Catalysts are also often used according to the invention. The catalysts may be of the kind already known per se, for example tertiary amines such as triethylene, tributyl-amine, N-methylmorpholine, N-ethylmorpholine, N-cocomorpholine, N,N,N',N'-tetramethyl-ethylenediamine, 1,4-diaza-bicyclo-(2,2,2)-octane, N-methyl-N'-dimethylaminoethylpiperazine, N,N-dimethylbenzylamine, bis-(N,N-diethylaminoethyl)-adipate, N,N-diethylbenzylamine, pentamethyl diethylene-triamine N,N-dimethylcyclohexylamine, N,N,N',N'-tetramethyl-1,3-butanediamine, N,N-dimethyl-β-phenylethylamine, 1,2-dimethylimidazole and 2-methylimidazole. Known Mannich bases of secondary amines such as dimethylamine and aldehydes, preferably formaldehyde; or ketones such as acetone, methyl ethyl ketone or cycohexanone and phenols such as phenol, nonylphenol or bis-phenol may also be used as catalysts.

Suitable catalysts in the form of tertiary amines which contain hydrogen atoms capable of reacting with isocyanate groups include e.g. triethanolamine, triisopropanolamine, N-methyl-diethanolamine, N-ethyl-diethanolamine and N,N-dimethyl-ethanolamine as well as their reaction products with ethylene oxides such as propylene oxide and/or ethylene oxide.

Silaamines containing carbon-silicon bonds as described in U.S. Pat. No. 3,620,984 may also be used as catalysts including 2,2,4-trimethyl-2-silamorpholine or 1,3-diethylaminomethyl-tetramethyl-disiloxane.

Bases which contain nitrogen, such as tetraalkylammonium hydroxides, or alkali metal hydroxides such as sodium hydroxide, alkali metal phenolates such as sodium phenolate or alkali metal alcoholates such as sodium methylate may also be used as catalysts. Hexahydrotriazines are also suitable catalysts.

Organic metal compounds may be used as catalysts according to the invention, in particular organic tin compounds.

The organic tin compounds used are preferably tin-(II) salts of carboxylic acids, such as tin(II) acetate, tin(II) octoate, tin(II) ethyl hexoate and tin(II) laurate and the tin(IV) compounds such as dibutyl tin oxide, dibutyl tin dichloride, dibutyl tin diacetate, dibutyl tin dilaurate, dibutyl tin maleate or dioctyl tin diacetate. Any of the above mentioned catalysts may, of course, also be used as mixtures.

Other examples of catalysts which may be used according to the invention and details concerning their activity may be found in Kunststoff-Handbuch, Volume VII, published by Vieweg and Hochtlen, Carl-Hanser-Verlag, Munich 1966, e.g. on pages 96 to 102.

The catalysts are generally used in a quantity of between about 0.001 and 10% by weight, based on the quantity of compounds having a molecular weight of 400 to 10,000 which contain at least two hydrogen atoms capable of reacting with isocyanates.

Surface active additives such as emulsifiers and foam stabilizers may also be used according to the invention. Suitable emulsifiers include the sodium salts of ricinoleic sulphonates or salts of fatty acids with amines, such as oleic acid diethylamine or stearic acid diethanolamine. Alkali metal or ammonium salts of sulphonic acids such as dodecylbenzene sulphonic acid or dinaphthylmethane disulphonic acid or salts of fatty acids such as ricinoleic acid or of polymeric fatty acids may also be used as surface active additives.

The foam stabilizers used are mainly polyether siloxanes, especially those which are water-soluble. These compounds generally have a polydimethylsiloxane group attached to a copolymer of ethylene oxide and propylene oxide. Foam stabilizers of this kind have been described in U.S. Pat. Nos. 2,834,748; 2,917,480 and 3,629,308.

Reaction retarders, e.g. substances which are acidic in reaction such as hydrochloric acid or organic acid halides; and cell regulators known per se such as paraffins or fatty alcohols or dimethylpolysiloxanes, pigments or dyes; stabilizers against ageing and weathering; plasticizers, fungistatic and bacteriostatic substances and fillers such as barium sulphate, kieselguhr, carbon black or whiting may also be used according to the invention.

Other examples of surface active additives, foam stabilizers, cell regulators, reaction retarders, stabilizers, plasticizers, dyes, fillers and fungistatic and bacteriostatic substances which may be used according to the invention and details concerning methods of using these additives and their mode of action are described in Kunststoff-Handbuch, Volume VII, published by Vieweg and Hochtlen, Carl-Hanser-Verlag, Munich 1966, e.g. on pages 103 to 113.

According to the invention, the components are reacted together by the known one-step process, prepolymer process or semiprepolymer process, in many cases using mechanical devices such as those described in U.S. Pat. No. 2,764,565. Details concerning processing apparatus which may also be used in the invention may be found in Kunststoff-Handbuch, Volume VII, published by Vieweg and Höchtlen, Carl-Hanser-Verlag, Munich 1966, e.g. on pages 121 to 205.

According to the invention, production of the foam is in many cases carried out by foaming inside molds. In this method, the reaction mixture is introduced into a mold which may be made of a metal such as aluminium, or a synthetic resin such as an epoxide resin. The reaction mixture foams up inside the mold to form the molded product. Foaming in the mold may either be carried out in such a way that the molded product obtained has a cellular structure on its surface or it may be carried out to produce a molded product with a compact skin and cellular core. In other words, the reaction mixture may either be introduced into the mold in a quantity just sufficient to enable the resulting foam to fill the mold or it may be introduced in a larger quantity, in which case foaming is said to be carried out under conditions of overcharging, a procedure which has already been disclosed, in e.g. U.S. Pat. Nos. 1,178,490 and 3,182,104.

So-called external mold release agents, such as silicone oils, are frequently used for foaming in the mold, but if desired, so-called internal mold release agents of this kind disclosed in German Offenlegungsschriften Nos. 2,121,670 and 2,307,589 may be used, if desired together with external mold release agents.

Cold setting foams may also be produced according to the invention (see, e.g., British Pat. No. 1,162,517 and German Offenlegungsschriften No. 2,153,086).

Foams may, of course, also be produced by the process of block foaming or by the double conveyor belt process which is known per se.

The following Examples serve to explain the present invention. The parts and percentages given represent parts by weight or percentages by weight unless otherwise indicated.

EXAMPLE 1

2-Diethanolamino-4,6-bis-(diethoxyphosphono)-s-triazine 184.4 g (1 mol) of cyanuric chloride are suspended in 300 ml of partly distilled toluene and heated to 90° C. 332 g (2 mol) of triethylphosphite are added dropwise during 3½ hours with stirring. A slight temperature rise is observed during this time. The reaction mixture is then heated under reflux for 1½ hours. A gas meter attached to the apparatus indicated an ethyl chloride volume of 42.2 l at 20° C.

When the reaction mixture has cooled to room temperature, 210 g (2 mol) of diethanolamine are added dropwise after it has been mixed with 20 ml of methylene chloride to prevent any recrystallization in the dropping funnel. The reaction temperature is kept within the range of 25° to 40° C by cooling with water. The mixture is then stirred for 1½ hours at room temperature and the toluene is drawn off in a water jet vacuum at 60° C. The residue is taken up with 1½ liters of methylene chloride, and the hydrochloride of diethanolamine is extracted with a small quantity of water. The aqueous phase is reextracted with methylene chloride and finally the total quantity of methylene chloride is evaporated off in a high vacuum. An orange colored oil remains behind.

Yield: 402 g = 87.8% of the theory (based on cyanuric chloride). The structure of this substance is confirmed by the following spectroscopic data:

Identified bands in the IR spectrum: OH (3375 cm$^{-1}$), P=O (1240 cm$^{-1}$), PO-alkyl (1010 cm$^{-1}$), $^1$H—NMR (in CDCl$_3$): $\delta$ = 1.4 ppm: Triplet corresponding to the CH$_3$ of the diethoxyphosphono group $\delta$ = 3.85 ppm: Pseudosinglet (multiplet which is not broken up) of the N—CH$_2$—CH$_2$—O group $\delta$ = 4.45 ppm: Multiplet (5 lines) belonging to the CH$_2$ of the diethoxyphosphono groups (split up by the P-atom)

$\delta$ = 4.6 ppm: singlet of the OH group (exchangeable by addition of D$_2$O).

EXAMPLE 2

2-[Di-(2'-hydroxypropyl)-amino]-4,6-bis-(diethoxyphosphono)-s-triazine (a) 184.4 g (1 mol) of cyanuric chloride in 300 ml of toluene (partly distilled) are reacted with 332 g (2 mol) of triethylphosphite and 226 g (2 mol) of di-(2-hydroxypropyl) amine as described in Example 1.

Yield: 442 g of an orange colored oil.

A sample of this oil dissolved in toluene and precipitated with petroleum ether gives the following results on analysis:

Calculated: C 42.4% H 7.1% N 11.5% P 12.8%
Found: C 42.5% H 7.3% N 11.5% P 12.8%

(b) 184.4 g (1 mol) of cyanuric chloride in 300 ml of partly distilled 1,2-dichloroethane are reacted with 332 g (2 mol) of triethylphosphite and 226 g (2 mol) of di-(2-hydroxypropyl)-amine as described in Example 1. After extraction of the hydrochloride and evaporation of dichloroethane, an orange colored oil remains behind, the IR data of which agree with those of the oil described under 2(a).

EXAMPLE 3

2-(2'-Methoxy-ethoxy)-4-[di-(2'-hydroxypropyl)-amino]-6-diethoxyphosphono-s-triazine 224 g (1 mol) of 2-(2'-methoxy-ethoxy)-4,6-dichloro-s-triazine are heated under reflux in 300 ml of partly distilled 1,2-dichloroethane, and 166 g (1 mol) of triethylphosphite are added dropwise during 2½ hours. The reaction ceases after the evolution of 18.2 l of gaseous ethyl chloride.

226 g (2 mol) of di-(2-hydroxypropyl)-amine are added to the clear solution during 2½ hours under conditions of cooling with water so that the reaction temperature does not exceed 45° C. Stirring in continued for a further 2 hours at room temperature and the hydrochloride is then extracted with water and dichloroethane is evaporated off under vacuum. The product, a yellowish oil, weighs 290 g.

The $^1$H-NMR spectrum shows the following data (taken in CDCl$_3$):

$\delta$ = 1.35 ppm: Multiplet (8 lines), belonging to the CH$_3$ of the hydroxypropyl- and ethoxy- groups.

$\delta$ = 3.4 ppm: Singlet of the methoxy group $\delta$ = 4.7 ppm: Singlet of the OH groups The signals of the remaining H atoms are found in the region of $\delta$ = 3.1–4.65; they consist of two multiplet groups.

EXAMPLE 4

2,4-Bis-(N-Methyl-ethanolamino)-6-diethoxyphosphono-s-triazine 184.4 g (1 mol) of cyanuric chloride are suspended in 300 ml of partly distilled 1,2-dichloroethane and heated to reflux. 166 g (1 mol) of triethylamine are added dropwise during 2½ hours. When 21.11 l of gaseous ethyl chloride have evolved, the reaction mixture is cooled to room temperature and 300.5 g (4 mol) of N-methylethanolamine are added dropwise under conditions of cooling with water so that the reaction temperature does not rise above 45° C. Stirring is then continued for 3 hours at 45° C. The amine hydrochloride is removed from the organic phase by extraction with water while the dichloroethane phase is concentrated by evaporation. A viscous, yellowish oil remains behind. Yield: 236 g (65% of the theory, based on cyanuric chloride) $^1$H-NMR data (CDCl$_3$):

$\delta$ = 1.35 ppm: Triplet, corresponding to the CH$_3$ of the diethoxyphosphono group $\delta$ = 3.15 ppm: Singlet of the N—CH$_3$ groups $\delta$ = 3.7 ppm: Pseudosinglet from N—CH$_2$—CH$_2$—O $\delta$ = 4.3 ppm: Multiplet (5 lines) of the methylene groups (diethoxyphosphono group)

The singlet signal of the OH groups is superimposed on this multiplet: $\delta$ = 4.15 ppm.

EXAMPLE 5

2-[Di-(2'-Hydroxypropyl)-amino]-4-diethylamino-6-diethoxyphosphono-s-triazine 184.4 g (1 mol) of cyanuric chloride are heated to reflux in 300 ml of partly distilled 1,2-dichloroethane. 166 g (1 mol) of triethylphosphite are added dropwise during 2 hours. The reaction mixture is then stirred until a gas meter attached to the apparatus indicates that 20.2 l of gaseous ethyl chloride have been evolved. 266.4 g (2 mol) of di-(2-hydroxypropyl)-amine are added dropwise at room temperature during 2 hours, the temperature being controlled so that it does not rise above 45° C, and the mixture is then stirred for a further 3½ hours at 40° C. The amine hydrochloride is then removed from the organic phase by extraction with water at room temperature. The dichloroethane phase is evaporated under vacuum and the oil which remains behind, amounting to 324 g (0.884 mol of intermediate product) is dissolved in 300 ml of dichloroethane.

122.6 g (1.76 mol) of diethylamine are then added to this solution during one hour. The solution is then stirred for 2½ hours at 45° C.

Yield: 240 g of yellow oil (57.3% based on cyanuric chloride) $^1$H-NMR data (CDCl$_3$):

$\delta$ = 1.3 ppm: Multiplet (7 lines) due to the CH$_3$ of the diethylamino, diethoxyphosphono and hydroxypropyl group. The signals of the other hydrogen atoms (two multiplets with 5 lines each) are found in the region of $\delta$ = 3.3–4.3 ppm;

$\delta$ = 5.1 ppm singlet of the OH group.

EXAMPLE 6

2-[Di-(2'-hydroxypropyl)-amino]-4-methyl-6-diethoxyphosphono-s-triazine 164 g (1 mol) of 2-methyl-4,6-dichloro-s-triazine are suspended in 280 ml of partly distilled 1,2-dichloroethane and heated to reflux. 166 g (1 mol) of triethylphosphite are then added dropwise during 2½ hours. When 21.2 l of gaseous ethyl chloride have been evolved, the reaction mixture is left to cool to room temperature and 266 g (2 mol) of di-(2-hydroxypropyl)amine are then added at such a rate that the reaction temperature does not rise above 45° C. (Time taken for additional 2¼ hours). After the reaction mixture has been stirred for a further 2 hours, the amine hydrochloride is extracted with water and the dichloroethane phase is evaporated under vacuum. Yield: 195 g (53.9%, based on methyl-dichloro-s-triazine); yellow oil. A sample of this oil dissolved in toluene and precipitated with petroleum ether is found to have the following structural data in the $^1$H-NMR spectrum (CDCl$_3$):

$\delta$ = 1.15 ppm: Multiplet (5 lines) belonging to the CH$_3$ of the hydroxypropyl and ethoxy groups $\delta$ = 2.4 ppm: Singlet of the 4-methyl group $\delta$ = 5.0 ppm: Singlet of the OH groups The signals of the remaining H atoms (two multiplets) are situated in the range of $\delta$ = 3.5–4.6 ppm.

EXAMPLE 7

Compound A 22 g of a polyether polyol prepared by the addition of propylene oxide to trimethylolpropane (OH number 850), 15 g of a polyether polyol prepared by successive addition of propylene oxide and ethylene oxide to trimethylol propane (OH number 42), 10 g of monofluorotrichloromethane, 0.5 g of a commercial polyether polysiloxane foam stabilizer (OS 50 of Bayer AG)

2.5 g of dimethylbenzylamine, 0.3 g of tetramethylguanidine, 50 g of the compound according to Example 1.

Compound B 83 g of a commercial crude 4,4'-diisocyanatodiphenylmethane (NCO content 31.3%).

The constituents of Component A are weighed in together and vigorously mixed. Component B is then stirred in and the finished reaction mixture is introduced into a temperature controlled aluminum mold which is at 60° C. The reaction mixture begins to foam after 40 seconds (measured from the moment when Components A and B have been stirred together). It fills the mold under a foaming pressure and then hardens. After 15 minutes, a hardened integral foam plate 10 mm in thickness can be removed from the mold. It has a gross density of 0.54 g/cm$^3$ and contains 4% of bound phosphorus, based on the cross-linked resin mass. Test for fire resistance:

(1) According to UL-Subj. 94 (V text).
   Total after-burning time in 5 × 2 flame tests: 24 seconds
   Classification: UL-VO
(2) According to CSA C 22.2/No. 1–64 Section 6, 13
   Classification: passed
   After-burning time: 1, 7, 12, 9, 23 seconds.

EXAMPLE 8

Component A 45 g of a polyether polyol (trimethylolpropane, chain lengthened with propylene oxide, OH number 850),
30 g of a polyether polyol (trimethylolpropane, chain lengthened with propylene oxide and ethylene oxide, OH number 42),
10 g of monofluorotrichloromethane,
0.5 g of a polyether polysiloxane foam stabilizer (OS 50 of Bayer AG)
3.5 g of dimethylbenzylamine,
0.5 g of tetramethylguanidine,
37 g of the compound according to Example 2.

Component B 123 g of the diisocyanate used in Example 7.

The reaction mixture is prepared and worked up as in Example 5. It begins to foam after 32 seconds. A foam plate 10 mm in thickness can be removed from the mold after 12 minutes. Its density is 0.51 g/cm$^3$, its phosphorus content 2%.

TESTS FOR FIRE RESISTANCE (1) According to UL-Subj. 94
   Total after burning time: 6 seconds;
   Classification: UL-VO
(2) CSA test
   After burning times: 1, 4, 10, 20, 6 seconds;
   Classification: passed.

Comparison Example

If the process is carried out as described in Example 7 or 8 but without the compounds according to the invention, the material passes neither the fire test according to UL-Subj. 94 nor the CSA test.

EXAMPLE 9

A mixture of
100 parts by weight of a polypropylene glycol having an OH number of 28 which has been started on trimethylolpropane and modified with ethylene oxide so that it contains 60% of primary hydroxyl end groups
3.1 parts by weight of water,
0.2 parts by weight of diazabicyclo-2,2,2-octane,
0.5 parts by weight of N-methylmorpholine,
0.5 parts by weight of N,N-dimethylethanolamine,
1.0 part by weight of a silicone stabilizer according to the general Formula:

$$R_3-SiO-\left[\begin{array}{c}R' \\ | \\ Si-O \\ | \\ O \\ | \\ SiR_3\end{array}\right]_a-SiR_3$$

R = CH$_3$
R' = phenyl
a = 0 to 4

2.0 parts by weight of the compound described in Example 1 and
45.0 parts by weight of the isocyanate described below is reacted in a closed mold.

20 Parts of 1,2-propylene glycol are added to a mixture of 225 parts of a mixture of 80% by weight of 2,4- and 20% by weight of 2,6-tolylene diisocyanate and 274 parts of 4,4'-diphenylmethane diisocyanate at 60° C and the mixture is reacted inside a metal mold for 30 minutes. After the addition of 1 part of β-phenylethyl-ethylene imine, the mixture is heated to 130° C. The trimerization reaction which takes place at this temperature is stopped by the addition of 1 part of p-toluenesulphonic acid methyl ester after 2½ hours, when the NCO content of the reaction mixture is 26.5%.

After dilution with 624 parts of an 80/20 mixture of 2,4- and 2,6-tolylene diisocyanate, a polyisocyanate is obtained which has an NCO content of 38.4% by weight, a viscosity of 24 cP at 25° C and a refractive index $n_D^{50}$ = 1.5738.

A foam which has the following mechanical properties is obtained.

| | | |
|---|---|---|
| Gross density | (DIN 53420) | 34 kg/m$^3$ |
| Tensile test | (DIN 53571) | 85 KPa |
| Elongation at break | (DIN 53571) | 150% |
| Compression test | (DIN 53577) | 2.3 KPa |
| Pressure deformation residue | (DIN 53572) | 63% |

Fire Test According to ASTM-D 1692–68

Assessment: self extinguishing
Average length of burning path: 70 mm
Average extinction time: 44 seconds

What is claimed is:
1. In a process for the production of polyurethane resins comprising reacting polyisocyanate, high molecular and/or low molecular weight polyols, and optionally other compounds containing groups which are reactive with isocyanates, the improvement which comprises using as compounds which contain groups capable of reacting with isocyanates in such a quantity that the polyurethane contains at least 0.5% by weight of phosphorus, the compounds of the general formula:

[chemical structure showing a triazine ring with substituents R$_2$, R$_1$-OH, N, R$_3$, P=O, A, L]

wherein

R₁ represents $C_1$–$C_5$ alkylene groups which may be branched,

R₂ represents $C_1$–$C_3$ alkyl groups which may be branched or R₁OH and

R₃ represents $C_1$–$C_8$-alkyl, $C_1$–$C_8$-dialkylamino, $C_1$–$C_4$-oxyalkyl, $C_1$–$C_4$-thioalkyl, $C_6$–$C_{14}$-aryl or $C_7$–$C_{15}$-aralkyl groups or

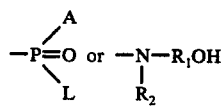

and

A and L may be identical or different and represent $C_1$–$C_{10}$-alkyl groups, which may be branched, benzyl groups or OR groups, wherein R represents an alkyl group, with 1–8 C atoms which may be branched, or a benzyl group.

2. The process of claim 1 wherein said compound of the general formula is:

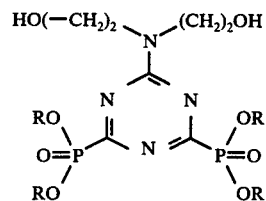

wherein
R represents an ethyl or propyl group.

3. The process of claim 1 wherein said compound of the general formula is:

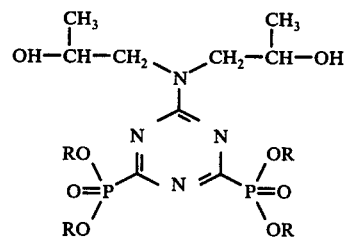

wherein
R represents an ethyl or propyl group.

4. The polyurethane resins produced by the process of claim 1.

5. The polyurethane resins prepared by the process of claim 2.

6. The polyurethane resin produced by the process of claim 3.

* * * * *